US012589238B2

(12) United States Patent
Vollmer

(10) Patent No.: US 12,589,238 B2
(45) Date of Patent: Mar. 31, 2026

(54) ROTOR, MAGNETIC COUPLING DEVICE, ELECTRIC MOTOR FOR A CARDIAC SUPPORT SYSTEM, PUMP UNIT FOR A CARDIAC SUPPORT SYSTEM, AND METHOD FOR PRODUCING A ROTOR

(71) Applicant: KARDION GMBH, Stuttgart (DE)

(72) Inventor: Uwe Vollmer, Sindelfingen (DE)

(73) Assignee: KARDION GMBH, Stuttgart (DE)

( * ) Notice: Subject to any disclaimer, the term of this patent is extended or adjusted under 35 U.S.C. 154(b) by 1477 days.

(21) Appl. No.: 17/055,023

(22) PCT Filed: May 16, 2019

(86) PCT No.: PCT/EP2019/062745
§ 371 (c)(1),
(2) Date: Jun. 11, 2021

(87) PCT Pub. No.: WO2019/219882
PCT Pub. Date: Nov. 21, 2019

(65) Prior Publication Data
US 2021/0322756 A1     Oct. 21, 2021

(30) Foreign Application Priority Data
May 16, 2018     (DE) ..................... 10 2018 207 594.8

(51) Int. Cl.
*A61M 60/492* (2021.01)
*A61M 60/216* (2021.01)
(Continued)

(52) U.S. Cl.
CPC ........ *A61M 60/492* (2021.01); *A61M 60/216* (2021.01); *A61M 60/419* (2021.01); *A61M 60/804* (2021.01)

(58) Field of Classification Search
None
See application file for complete search history.

(56) References Cited

U.S. PATENT DOCUMENTS

| | | | |
|---|---|---|---|
| 2,254,698 A | 9/1941 | Hansen, Jr. | |
| 2,310,923 A | 2/1943 | Bean | |
| (Continued) | | | |

FOREIGN PATENT DOCUMENTS

| | | |
|---|---|---|
| AU | 7993698 | 2/1999 |
| AU | 2002308409 | 12/2005 |
| (Continued) | | |

OTHER PUBLICATIONS

International Search Report for International Application No. PCT/EP2019/062742 dated Jul. 17, 2019.
(Continued)

*Primary Examiner* — Erica S Lee
(74) *Attorney, Agent, or Firm* — Knobbe, Martens, Olson & Bear, LLP

(57) ABSTRACT

A rotor for a cardiac support system is disclosed. The rotor is assembled or can be assembled from at least four shell elements to form a hollow cylinder and/or on a shaft, wherein the shell elements are magnetized or can be magnetized alternately in magnetization direction which are oppositely directed or are orthogonal, so as to form a magnetized body having at least four magnetic poles.

15 Claims, 5 Drawing Sheets

(51) Int. Cl.
 *A61M 60/419* (2021.01)
 *A61M 60/804* (2021.01)

(56) References Cited

U.S. PATENT DOCUMENTS

| | | | |
|---|---|---|---|
| 3,085,407 A | 4/1963 | Tomlinson | |
| 3,505,987 A | 4/1970 | Heilman | |
| 3,568,659 A | 3/1971 | Karnegis | |
| 3,614,181 A | 10/1971 | Meeks | |
| 3,747,998 A | 7/1973 | Klein et al. | |
| 3,807,813 A | 4/1974 | Milligan | |
| 3,995,617 A | 12/1976 | Watkins et al. | |
| 4,115,040 A | 9/1978 | Knorr | |
| 4,245,622 A | 1/1981 | Hutchins, IV | |
| 4,471,252 A | 9/1984 | West | |
| 4,522,194 A | 6/1985 | Normann | |
| 4,625,712 A | 12/1986 | Wampler | |
| 4,643,641 A | 2/1987 | Clausen et al. | |
| 4,753,221 A | 6/1988 | Kensey et al. | |
| 4,779,614 A | 10/1988 | Moise | |
| 4,785,795 A | 11/1988 | Singh et al. | |
| 4,817,586 A | 4/1989 | Wampler | |
| 4,846,152 A | 7/1989 | Wampler et al. | |
| 4,888,011 A | 12/1989 | Kung et al. | |
| 4,889,131 A | 12/1989 | Salem et al. | |
| 4,895,557 A | 1/1990 | Moise et al. | |
| 4,896,754 A | 1/1990 | Carlson et al. | |
| 4,902,272 A | 2/1990 | Milder et al. | |
| 4,908,012 A | 3/1990 | Moise et al. | |
| 4,927,407 A | 5/1990 | Dorman | |
| 4,943,275 A | 7/1990 | Stricker | |
| 4,944,722 A | 7/1990 | Carriker et al. | |
| 4,968,300 A | 11/1990 | Moutafis et al. | |
| 4,971,768 A | 11/1990 | Ealba | |
| 4,985,014 A | 1/1991 | Orejola | |
| 5,044,897 A | 9/1991 | Dorman | |
| 5,061,256 A | 10/1991 | Wampler | |
| 5,089,016 A | 2/1992 | Millner et al. | |
| 5,090,957 A | 2/1992 | Moutafis et al. | |
| 5,112,292 A | 5/1992 | Hwang et al. | |
| 5,112,349 A | 5/1992 | Summers et al. | |
| 5,116,305 A | 5/1992 | Milder et al. | |
| 5,195,877 A | 3/1993 | Kletschka | |
| 5,290,227 A * | 3/1994 | Pasque | A61M 60/422 |
| | | | 623/3.13 |
| 5,297,940 A | 3/1994 | Buse | |
| 5,313,765 A | 5/1994 | Martin | |
| 5,344,443 A | 9/1994 | Palma et al. | |
| 5,354,271 A | 10/1994 | Voda | |
| 5,376,114 A | 12/1994 | Jarvik | |
| 5,399,145 A | 3/1995 | Ito et al. | |
| 5,405,383 A | 4/1995 | Barr | |
| 5,443,503 A | 8/1995 | Yamane | |
| 5,456,715 A | 10/1995 | Liotta | |
| 5,527,159 A | 6/1996 | Bozeman, Jr. et al. | |
| 5,599,173 A | 2/1997 | Chen et al. | |
| 5,613,935 A | 3/1997 | Jarvik | |
| 5,695,471 A | 12/1997 | Wampler | |
| 5,702,430 A | 12/1997 | Larson, Jr. et al. | |
| 5,720,771 A | 2/1998 | Snell | |
| 5,746,709 A | 5/1998 | Rom et al. | |
| 5,749,855 A | 5/1998 | Reitan | |
| 5,752,976 A | 5/1998 | Duffin et al. | |
| 5,766,207 A | 6/1998 | Potter et al. | |
| 5,831,365 A | 11/1998 | Keim et al. | |
| 5,888,241 A | 3/1999 | Jarvik | |
| 5,888,242 A | 3/1999 | Antaki et al. | |
| 5,904,646 A | 5/1999 | Jarvik | |
| 5,911,685 A | 6/1999 | Siess et al. | |
| 5,921,913 A | 7/1999 | Siess | |
| 5,964,694 A | 10/1999 | Siess et al. | |
| 6,001,056 A | 12/1999 | Jassawalla et al. | |
| 6,007,478 A | 12/1999 | Siess et al. | |
| 6,018,208 A | 1/2000 | Maher et al. | |
| 6,050,975 A | 4/2000 | Poirier | |
| 6,071,093 A | 6/2000 | Hart | |
| 6,116,862 A | 9/2000 | Rau et al. | |
| 6,123,659 A | 9/2000 | le Blanc et al. | |
| 6,135,710 A | 10/2000 | Araki et al. | |
| 6,149,405 A | 11/2000 | Abe et al. | |
| 6,155,969 A | 12/2000 | Schima et al. | |
| 6,158,984 A | 12/2000 | Cao et al. | |
| 6,161,838 A | 12/2000 | Balsells | |
| 6,176,848 B1 | 1/2001 | Rau et al. | |
| 6,186,665 B1 | 2/2001 | Maher et al. | |
| 6,210,318 B1 | 4/2001 | Lederman | |
| 6,217,541 B1 | 4/2001 | Yu | |
| 6,220,832 B1 | 4/2001 | Schob | |
| 6,227,820 B1 | 5/2001 | Jarvik | |
| 6,245,007 B1 | 6/2001 | Bedingham et al. | |
| 6,254,359 B1 | 7/2001 | Aber | |
| 6,264,205 B1 | 7/2001 | Balsells | |
| 6,264,601 B1 | 7/2001 | Jassawalla et al. | |
| 6,264,645 B1 | 7/2001 | Jonkman | |
| 6,293,752 B1 | 9/2001 | Clague et al. | |
| 6,351,048 B1 | 2/2002 | Schob et al. | |
| 6,361,292 B1 | 3/2002 | Chang et al. | |
| 6,432,136 B1 | 8/2002 | Weiss et al. | |
| 6,445,956 B1 | 9/2002 | Laird et al. | |
| 6,447,266 B2 | 9/2002 | Antaki et al. | |
| 6,527,698 B1 | 3/2003 | Kung et al. | |
| 6,530,876 B1 | 3/2003 | Spence | |
| 6,533,716 B1 | 3/2003 | Schmitz-Rode et al. | |
| 6,540,658 B1 | 4/2003 | Fasciano et al. | |
| 6,544,216 B1 | 4/2003 | Sammler et al. | |
| 6,579,257 B1 | 6/2003 | Elgas et al. | |
| 6,592,620 B1 | 7/2003 | Lancisi et al. | |
| 6,595,743 B1 | 7/2003 | Kazatchkov et al. | |
| 6,607,368 B1 | 8/2003 | Ross et al. | |
| 6,623,475 B1 | 9/2003 | Siess | |
| 6,719,791 B1 | 4/2004 | Nüsser et al. | |
| 6,794,789 B2 | 9/2004 | Siess et al. | |
| 6,841,910 B2 | 1/2005 | Gery | |
| 6,879,126 B2 | 4/2005 | Paden et al. | |
| 6,912,423 B2 | 6/2005 | Ley et al. | |
| 6,942,611 B2 | 9/2005 | Siess | |
| 6,949,066 B2 | 9/2005 | Bearnson et al. | |
| 6,969,345 B2 | 11/2005 | Jassawalla et al. | |
| 7,011,620 B1 | 3/2006 | Siess | |
| 7,014,620 B2 | 3/2006 | Kim | |
| 7,022,100 B1 | 4/2006 | Aboul-Hosn et al. | |
| 7,027,875 B2 | 4/2006 | Siess et al. | |
| 7,070,398 B2 | 7/2006 | Olsen et al. | |
| 7,070,555 B2 | 7/2006 | Siess | |
| 7,083,588 B1 | 8/2006 | Shmulewitz et al. | |
| 7,144,364 B2 | 12/2006 | Barbut et al. | |
| 7,160,243 B2 | 1/2007 | Medvedev | |
| 7,238,151 B2 | 7/2007 | Frazier | |
| 7,241,257 B1 | 7/2007 | Ainsworth et al. | |
| 7,264,606 B2 | 9/2007 | Jarvik et al. | |
| 7,393,181 B2 | 7/2008 | McBride et al. | |
| 7,462,019 B1 | 12/2008 | Allarie et al. | |
| 7,479,102 B2 | 1/2009 | Jarvik | |
| 7,502,648 B2 | 3/2009 | Okubo et al. | |
| 7,736,296 B2 | 6/2010 | Siess et al. | |
| 7,762,941 B2 | 7/2010 | Jarvik | |
| 7,798,952 B2 | 9/2010 | Tansley et al. | |
| 7,841,976 B2 | 11/2010 | McBride et al. | |
| 7,850,593 B2 | 12/2010 | Vincent et al. | |
| 7,878,967 B1 | 2/2011 | Khanal | |
| 7,914,436 B1 | 3/2011 | Kung | |
| 7,934,909 B2 | 5/2011 | Nuesser et al. | |
| 7,959,551 B2 | 6/2011 | Jarvik | |
| 7,963,905 B2 | 6/2011 | Salmonsen et al. | |
| 7,998,190 B2 | 8/2011 | Gharib et al. | |
| 8,012,079 B2 | 9/2011 | Delgado, III | |
| 8,075,472 B2 | 12/2011 | Zilbershlag et al. | |
| 8,088,059 B2 | 1/2012 | Jarvik | |
| 8,114,008 B2 | 2/2012 | Hidaka et al. | |
| 8,123,669 B2 | 2/2012 | Siess et al. | |
| RE43,299 E | 4/2012 | Siess | |
| 8,152,845 B2 | 4/2012 | Bourque | |
| 8,177,703 B2 | 5/2012 | Smith et al. | |
| 8,216,122 B2 | 7/2012 | Kung | |

(56)                References Cited

U.S. PATENT DOCUMENTS

| | | |
|---|---|---|
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,474,840 B2 | 10/2016 | Siess |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,314 B2 | 2/2017 | Aboul-Hosn et al. |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,717,833 B2 | 8/2017 | McBride et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,773,002 B2 | 9/2020 | Siess et al. |

(56) References Cited

U.S. PATENT DOCUMENTS

| 10,780,208 B2 | 9/2020 | Siess et al. |
| 10,814,053 B2 | 10/2020 | Throckmorton et al. |
| 10,857,273 B2 | 12/2020 | Hodges et al. |
| 10,864,308 B2 | 12/2020 | Muller et al. |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |

(56) References Cited

U.S. PATENT DOCUMENTS

| | | | |
|---|---|---|---|
| 11,668,321 B2 | 6/2023 | Richert et al. |
| 11,674,517 B2 | 6/2023 | Mohl |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,744,987 B2 | 9/2023 | Siess et al. |
| 11,745,005 B2 | 9/2023 | Delgado, III |
| 11,746,906 B1 | 9/2023 | Balta et al. |
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,551 B2 | 10/2023 | Yanai et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,443 B2 | 11/2023 | Hanson et al. |
| 11,813,444 B2 | 11/2023 | Siess et al. |
| 11,819,678 B2 | 11/2023 | Siess et al. |
| 11,826,127 B2 | 11/2023 | Casas |
| 11,833,278 B2 | 12/2023 | Siess et al. |
| 11,833,342 B2 | 12/2023 | Tanner et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| 11,857,743 B2 | 1/2024 | Fantuzzi et al. |
| 11,857,777 B2 | 1/2024 | Earles et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| 11,890,212 B2 | 2/2024 | Gilmartin et al. |
| 11,896,482 B2 | 2/2024 | Delaloye et al. |
| 11,898,642 B2 | 2/2024 | Stanton et al. |
| 11,904,104 B2 | 2/2024 | Jahangir |
| 11,911,579 B2 | 2/2024 | Tanner et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,938,311 B2 | 3/2024 | Corbett et al. |
| 11,944,805 B2 | 4/2024 | Stotz |
| 11,957,892 B2 | 4/2024 | Siess et al. |
| 11,980,385 B2 | 5/2024 | Haselman |
| 11,986,604 B2 | 5/2024 | Siess |
| 12,005,248 B2 | 6/2024 | Vogt et al. |
| 12,011,583 B2 | 6/2024 | Wang |
| 12,017,058 B2 | 6/2024 | Kerkhoffs et al. |
| 12,023,476 B2 | 7/2024 | Tuval et al. |
| 12,023,477 B2 | 7/2024 | Siess |
| 12,059,559 B2 | 8/2024 | Muller et al. |
| 12,064,120 B2 | 8/2024 | Hajjar et al. |
| 12,064,611 B2 | 8/2024 | D'Ambrosio et al. |
| 12,064,614 B2 | 8/2024 | Agah et al. |
| 12,064,615 B2 | 8/2024 | Stotz et al. |
| 12,064,616 B2 | 8/2024 | Spanier et al. |
| 12,076,544 B2 | 9/2024 | Siess et al. |
| 12,076,549 B2 | 9/2024 | Stotz et al. |
| 12,076,550 B2 | 9/2024 | Edwards et al. |
| 12,090,314 B2 | 9/2024 | Tuval et al. |
| 12,092,114 B2 | 9/2024 | Siess |
| 12,097,016 B2 | 9/2024 | Goldvasser |
| 12,102,815 B2 | 10/2024 | Dhaliwal et al. |
| 12,104,600 B2 | 10/2024 | Mohl |
| 12,107,474 B2 | 10/2024 | Vollmer |
| 12,117,007 B1 | 10/2024 | Mohl |
| 12,121,713 B2 | 10/2024 | Calomeni et al. |
| 12,133,976 B2 | 11/2024 | Malone et al. |
| 12,144,936 B2 | 11/2024 | Tao et al. |
| 12,144,976 B2 | 11/2024 | Baumbach et al. |
| 12,161,854 B2 | 12/2024 | Earles et al. |
| 12,161,855 B2 | 12/2024 | Hastie et al. |
| 12,161,857 B2 | 12/2024 | Saul et al. |
| 12,171,993 B2 | 12/2024 | Higgins et al. |
| 12,194,287 B2 | 1/2025 | Kassel et al. |
| 12,196,210 B2 | 1/2025 | Siess et al. |
| 12,201,823 B2 | 1/2025 | Baumbach et al. |
| 12,207,906 B2 | 1/2025 | Tuval et al. |
| 12,213,771 B2 | 2/2025 | Curran et al. |
| 12,233,251 B2 | 2/2025 | Siess et al. |
| 12,241,480 B2 | 3/2025 | Corbett et al. |
| 12,263,330 B2 | 4/2025 | D'Ambrosio et al. |
| 12,263,333 B2 | 4/2025 | Stotz et al. |
| 12,263,334 B2 | 4/2025 | Corbett et al. |
| 12,268,861 B2 | 4/2025 | D'Ambrosio et al. |
| 12,290,673 B2 | 5/2025 | Jahangir |
| 12,290,676 B2 | 5/2025 | Farago et al. |
| 12,303,678 B2 | 5/2025 | Kerkhoffs et al. |
| 12,303,680 B2 | 5/2025 | Siess et al. |
| 12,318,551 B2 | 6/2025 | Jahangir |
| 12,329,958 B2 | 6/2025 | Siess et al. |
| 12,337,163 B2 | 6/2025 | Radman |
| 12,343,516 B2 | 7/2025 | Cook |
| 12,343,518 B2 | 7/2025 | Tuval et al. |
| 12,343,519 B2 | 7/2025 | Siess et al. |
| 12,364,799 B2 | 7/2025 | Siess et al. |
| 12,364,850 B2 | 7/2025 | Siess et al. |
| 12,364,854 B2 | 7/2025 | Wang |
| 12,383,704 B2 | 8/2025 | Ship et al. |
| 12,383,724 B2 | 8/2025 | Kirchoff et al. |
| 12,383,727 B2 | 8/2025 | Kassel et al. |
| 12,390,633 B2 | 8/2025 | Stotz et al. |
| 12,397,146 B2 | 8/2025 | Hart et al. |
| D1,092,716 S | 9/2025 | Bernazani |
| 12,409,311 B2 | 9/2025 | Jahangir et al. |
| 12,415,056 B2 | 9/2025 | Siess et al. |
| 12,420,076 B2 | 9/2025 | Spanier et al. |
| 12,420,079 B2 | 9/2025 | Das et al. |
| 12,434,060 B2 | 10/2025 | Tan et al. |
| 2001/0009645 A1 | 7/2001 | Noda |
| 2001/0041934 A1 | 11/2001 | Yamazaki et al. |
| 2002/0076322 A1 | 6/2002 | Maeda et al. |
| 2002/0082585 A1 | 6/2002 | Carroll et al. |
| 2002/0147495 A1 | 10/2002 | Petroff |
| 2002/0153664 A1 | 10/2002 | Schroeder |
| 2003/0060685 A1 | 3/2003 | Houser |
| 2003/0091450 A1 | 5/2003 | Davis et al. |
| 2003/0100816 A1 | 5/2003 | Siess |
| 2003/0111800 A1 | 6/2003 | Kreutzer |
| 2003/0139643 A1 | 7/2003 | Smith et al. |
| 2003/0191357 A1 | 10/2003 | Frazier |

(56) References Cited

U.S. PATENT DOCUMENTS

| 2003/0199727 A1 | 10/2003 | Burke |
| 2004/0044266 A1 | 3/2004 | Siess et al. |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0008509 A1 | 1/2005 | Chang |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2005/0254976 A1 | 11/2005 | Carrier et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |
| 2008/0306328 A1 | 12/2008 | Ercolani |
| 2009/0004037 A1 | 1/2009 | Ito |
| 2009/0112312 A1 | 4/2009 | Larose et al. |
| 2009/0138080 A1 | 5/2009 | Siess et al. |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0268017 A1 | 10/2010 | Siess |
| 2010/0298625 A1 | 11/2010 | Reichenbach et al. |
| 2011/0172505 A1 | 7/2011 | Kim |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2012/0029265 A1 | 2/2012 | LaRose |
| 2012/0035645 A1 | 2/2012 | Gross |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0245404 A1 | 9/2012 | Smith |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0053623 A1 | 2/2013 | Evans |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0030122 A1* | 1/2014 | Ozaki .................... H02K 21/16 |
| | | 310/71 |
| 2014/0051908 A1 | 2/2014 | Khanal et al. |
| 2014/0079557 A1 | 3/2014 | LaRose et al. |
| 2014/0107399 A1 | 4/2014 | Spence |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2014/0368942 A1* | 12/2014 | Harrell .................. H02K 49/10 |
| | | 359/896 |
| 2015/0031936 A1 | 1/2015 | LaRose et al. |
| 2015/0051435 A1 | 2/2015 | Siess et al. |
| 2015/0051438 A1 | 2/2015 | Taskin |
| 2015/0080743 A1 | 3/2015 | Siess |
| 2015/0099923 A1 | 4/2015 | Magovern et al. |
| 2015/0141842 A1 | 5/2015 | Spanier et al. |
| 2015/0171694 A1 | 6/2015 | Dallas |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0362017 A1 | 12/2015 | Bell |
| 2015/0365738 A1 | 12/2015 | Purvis et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0067395 A1 | 3/2016 | Jimenez et al. |
| 2016/0101224 A1* | 4/2016 | Akkerman .......... A61M 60/178 |
| | | 600/16 |
| 2016/0144089 A1 | 5/2016 | Woo et al. |
| 2016/0144166 A1 | 5/2016 | Decré et al. |
| 2016/0166747 A1 | 6/2016 | Frazier et al. |
| 2016/0184499 A1* | 6/2016 | Ricci .................. A61M 60/422 |
| | | 600/16 |
| 2016/0213828 A1 | 7/2016 | Sievers |
| 2016/0223086 A1 | 8/2016 | Balsells et al. |
| 2016/0256620 A1 | 9/2016 | Scheckel et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0043074 A1 | 2/2017 | Siess |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groß-HardtTim et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0232169 A1 | 8/2017 | Muller |
| 2017/0271971 A1 | 9/2017 | Riemay et al. |
| 2017/0274126 A1 | 9/2017 | Tamburino et al. |
| 2017/0317573 A1* | 11/2017 | Mueller ................ H02K 49/102 |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0093070 A1 | 4/2018 | Cottone |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0219452 A1 | 8/2018 | Boisclair |
| 2018/0221551 A1 | 8/2018 | Tanner et al. |
| 2018/0221553 A1* | 8/2018 | Taskin ................ A61M 60/178 |
| 2018/0228950 A1 | 8/2018 | Janeczek et al. |

(56)                    References Cited

U.S. PATENT DOCUMENTS

| | | |
|---|---|---|
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0256797 A1 | 9/2018 | Schenck et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303991 A1* | 10/2018 | Nüsser ................. A61M 60/422 |
| 2018/0311421 A1 | 11/2018 | Tuseth |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0333059 A1 | 11/2018 | Casas |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0199165 A1* | 6/2019 | Carson .................... H02K 7/09 |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0211847 A1 | 7/2019 | Walsh et al. |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0282746 A1 | 9/2019 | Judisch |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0261633 A1 | 8/2020 | Spanier |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0346678 A1 | 11/2021 | Baumbach et al. |
| 2021/0346680 A1 | 11/2021 | Vogt et al. |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0384812 A1 | 12/2021 | Vollmer et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0249829 A1 | 8/2022 | Edwards et al. |
| 2022/0323742 A1 | 10/2022 | Grauwinkel et al. |
| 2023/0001178 A1 | 1/2023 | Corbett et al. |
| 2023/0063798 A1 | 3/2023 | Edwards et al. |
| 2023/0079625 A1 | 3/2023 | Theran et al. |
| 2023/0105131 A1 | 4/2023 | Kerkhoffs et al. |
| 2023/0125439 A1 | 4/2023 | Malone et al. |
| 2023/0128328 A1 | 4/2023 | Malone et al. |
| 2023/0130285 A1 | 4/2023 | Malone et al. |
| 2023/0149691 A1 | 5/2023 | VanCamp et al. |
| 2023/0149692 A1 | 5/2023 | Larsen et al. |
| 2023/0158289 A1 | 5/2023 | Breidall et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0075277 A1 | 3/2024 | Schellenberg |
| 2024/0102475 A1 | 3/2024 | Schuelke et al. |
| 2024/0198084 A1 | 6/2024 | Stotz |
| 2024/0245902 A1 | 7/2024 | Schlebusch et al. |
| 2024/0269459 A1 | 8/2024 | Schellenberg et al. |

(56)         References Cited

U.S. PATENT DOCUMENTS

| | | | |
|---|---|---|---|
| 2024/0277998 | A1 | 8/2024 | Vogt et al. |
| 2024/0285935 | A1 | 8/2024 | Popov et al. |
| 2024/0335651 | A1 | 10/2024 | Mitze et al. |
| 2024/0399135 | A1 | 12/2024 | Stotz et al. |
| 2025/0032773 | A1 | 1/2025 | Baumbach et al. |
| 2025/0121177 | A1 | 4/2025 | West |
| 2025/0144397 | A1 | 5/2025 | Kassel et al. |
| 2025/0161660 | A1 | 5/2025 | Baumbach et al. |
| 2025/0170388 | A1 | 5/2025 | Kerkhoffs et al. |

FOREIGN PATENT DOCUMENTS

| | | | |
|---|---|---|---|
| AU | 2012261669 | | 1/2013 |
| AU | 2013203301 | | 5/2013 |
| AU | 2013273663 | | 1/2014 |
| BR | PI0904483-3 | | 7/2011 |
| CA | 2 026 692 | | 4/1992 |
| CA | 2 026 693 | | 4/1992 |
| CA | 2 292 432 | | 5/1998 |
| CA | 2 664 835 | | 2/2008 |
| CA | 2 796 357 | | 10/2011 |
| CA | 2 947 984 | | 11/2022 |
| CN | 1222862 | A | 7/1999 |
| CN | 1254598 | A | 5/2000 |
| CN | 1376523 | A | 10/2002 |
| CN | 2535055 | | 2/2003 |
| CN | 1118304 | C | 8/2003 |
| CN | 2616217 | | 5/2004 |
| CN | 1202871 | C | 5/2005 |
| CN | 1833736 | A | 9/2006 |
| CN | 200977306 | | 11/2007 |
| CN | 101112628 | | 1/2008 |
| CN | 101128168 | | 2/2008 |
| CN | 201150675 | | 11/2008 |
| CN | 101677812 | | 3/2010 |
| CN | 201437016 | | 4/2010 |
| CN | 201618200 | | 11/2010 |
| CN | 201658687 | | 12/2010 |
| CN | 201710717 | | 1/2011 |
| CN | 201894758 | | 7/2011 |
| CN | 102475923 | | 5/2012 |
| CN | 102545538 | | 7/2012 |
| CN | 202314596 | | 7/2012 |
| CN | 102743801 | | 10/2012 |
| CN | 103143072 | | 6/2013 |
| CN | 103845766 | | 6/2014 |
| CN | 103861162 | | 6/2014 |
| CN | 103915980 | | 7/2014 |
| CN | 203809157 | | 9/2014 |
| CN | 203842087 | | 9/2014 |
| CN | 104208763 | | 12/2014 |
| CN | 104208764 | | 12/2014 |
| CN | 203971004 | | 12/2014 |
| CN | 104274873 | | 1/2015 |
| CN | 204106671 | | 1/2015 |
| CN | 204219479 | | 3/2015 |
| CN | 103877630 | | 2/2016 |
| CN | 205215814 | | 5/2016 |
| CN | 103977464 | | 8/2016 |
| CN | 104162192 | | 9/2016 |
| CN | 104888293 | | 3/2017 |
| CN | 106512117 | | 3/2017 |
| CN | 104225696 | | 6/2017 |
| CN | 107019824 | | 8/2017 |
| CN | 206443963 | | 8/2017 |
| CN | 107281567 | | 10/2017 |
| CN | 104707194 | | 11/2017 |
| CN | 107921187 | | 4/2018 |
| CN | 105498002 | | 6/2018 |
| CN | 106310410 | | 7/2018 |
| CN | 106902404 | | 8/2019 |
| CN | 209790495 | | 12/2019 |
| CN | 110665079 | | 1/2020 |
| CN | 210020563 | | 2/2020 |
| CN | 111166948 | | 5/2020 |
| CN | 111166949 | | 5/2020 |
| CN | 215841206 | | 2/2022 |
| CN | 217828630 | | 11/2022 |
| CN | 218922664 | | 4/2023 |
| CN | 116077106 | | 5/2023 |
| CN | 116365757 | | 6/2023 |
| CN | 219250364 | | 6/2023 |
| CN | 116785582 | | 9/2023 |
| CN | 116551654 | | 11/2023 |
| CN | 116440404 | | 3/2024 |
| CN | 117018427 | | 3/2024 |
| CN | 117482377 | | 4/2024 |
| CN | 118320293 | | 7/2024 |
| CN | 118320294 | | 7/2024 |
| CN | 113769260 | | 9/2024 |
| CN | 118142074 | | 9/2024 |
| CN | 118681125 | | 9/2024 |
| CN | 118899971 | | 11/2024 |
| DE | 1 001 642 | | 1/1957 |
| DE | 1 165 144 | | 3/1964 |
| DE | 27 07 951 | | 9/1977 |
| DE | 26 24 058 | | 12/1977 |
| DE | 3 545 214 | | 7/1986 |
| DE | 41 05 278 | | 8/1992 |
| DE | 195 46 336 | | 5/1997 |
| DE | 695 01 834 | | 10/1998 |
| DE | 198 54 724 | | 5/1999 |
| DE | 198 21 307 | | 10/1999 |
| DE | 199 10 872 | | 10/1999 |
| DE | 199 56 380 | | 11/1999 |
| DE | 100 59 714 | | 5/2002 |
| DE | 103 45 694 | | 4/2005 |
| DE | 697 31 709 | | 4/2005 |
| DE | 101 55 011 | | 11/2005 |
| DE | 601 19 592 | | 9/2006 |
| DE | 11 2004 001 809 | | 11/2006 |
| DE | 20 2005 020 288 | | 6/2007 |
| DE | 10 2006 019 206 | | 10/2007 |
| DE | 10 2006 036 948 | | 2/2008 |
| DE | 10 2008 060 357 | | 6/2010 |
| DE | 10 2009 039 658 | | 3/2011 |
| DE | 20 2009 018 416 | | 8/2011 |
| DE | 10 2010 041 995 | | 4/2012 |
| DE | 10 2012 022 456 | | 5/2014 |
| DE | 10 2013 007 562 | | 11/2014 |
| DE | 10 2014 210 299 | | 12/2015 |
| DE | 10 2014 212 323 | | 12/2015 |
| DE | 11 2014 001 418 | | 12/2015 |
| DE | 10 2014 224 151 | | 6/2016 |
| DE | 10 2015 216 050 | | 2/2017 |
| DE | 10 2015 219 263 | | 4/2017 |
| DE | 10 2015 222 199 | | 5/2017 |
| DE | 20 2015 009 422 | | 7/2017 |
| DE | 10 2012 207 042 | | 9/2017 |
| DE | 10 2016 013 334 | | 4/2018 |
| DE | 10 2017 209 917 | | 12/2018 |
| DE | 10 2017 212 193 | | 1/2019 |
| DE | 10 2018 207 564 | | 11/2019 |
| DE | 10 2018 207 578 | | 11/2019 |
| DE | 10 2018 207 585 | | 11/2019 |
| DE | 10 2018 207 591 | | 11/2019 |
| DE | 10 2018 207 594 | | 11/2019 |
| DE | 10 2018 207 611 | | 11/2019 |
| DE | 10 2018 207 622 | | 11/2019 |
| DE | 10 2018 208 536 | | 12/2019 |
| DE | 10 2018 208 540 | | 12/2019 |
| DE | 10 2018 208 541 | | 12/2019 |
| DE | 10 2018 208 550 | | 12/2019 |
| DE | 10 2018 208 945 | | 12/2019 |
| DE | 10 2018 210 076 | | 12/2019 |
| DE | 10 2018 207 624 | | 1/2020 |
| DE | 10 2018 211 327 | | 1/2020 |
| DE | 10 2018 211 328 | | 1/2020 |
| DE | 10 2018 212 153 | | 1/2020 |
| DE | 10 2018 213 350 | | 2/2020 |
| DE | 10 2018 220 658 | | 6/2020 |
| DE | 10 2020 102 473 | | 8/2021 |
| DE | 11 2020 003 063 | | 3/2022 |
| DE | 11 2020 004 148 | | 6/2022 |

(56) References Cited

FOREIGN PATENT DOCUMENTS

| | | |
|---|---|---|
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 047 872 | 9/2010 |
| EP | 2 403 109 | 1/2012 |
| EP | 2 187 807 | 6/2012 |
| EP | 2 330 724 | 8/2012 |
| EP | 3 326 567 | 10/2014 |
| EP | 1 898 971 | 3/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 1 931 403 | 1/2017 |
| EP | 3 127 562 | 2/2017 |
| EP | 2 585 129 | 3/2017 |
| EP | 2 646 068 | 3/2017 |
| EP | 3 143 682 | 3/2017 |
| EP | 3 187 210 | 7/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 131 599 | 2/2019 |
| EP | 3 456 367 | 3/2019 |
| EP | 3 119 451 | 6/2019 |
| EP | 3 536 360 | 9/2019 |
| EP | 3 542 835 | 9/2019 |
| EP | 3 542 836 | 9/2019 |
| EP | 3 062 877 | 12/2019 |
| EP | 3 189 862 | 2/2020 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 738 | 12/2020 |
| EP | 3 069 740 | 12/2020 |
| EP | 3 131 597 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 808 404 | 4/2021 |
| EP | 3 821 938 | 5/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 914 330 | 12/2021 |
| EP | 3 928 825 | 12/2021 |
| EP | 3 556 409 | 1/2022 |
| EP | 3 624 868 | 1/2022 |
| EP | 3 955 985 | 2/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 4 039 320 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 4 137 193 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |

(56) References Cited

FOREIGN PATENT DOCUMENTS

| | | |
|---|---|---|
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 4 218 897 | 8/2023 |
| EP | 4 218 898 | 8/2023 |
| EP | 4 218 899 | 8/2023 |
| EP | 2 961 984 | 9/2023 |
| EP | 3 352 808 | 9/2023 |
| EP | 3 554 576 | 10/2023 |
| EP | 3 615 102 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 808 390 | 11/2023 |
| EP | 4 061 470 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 768 344 | 7/2024 |
| EP | 3 970 765 | 7/2024 |
| EP | 3 854 444 | 9/2024 |
| EP | 4 384 259 | 9/2024 |
| EP | 4 429 750 | 9/2024 |
| EP | 3 534 985 | 10/2024 |
| EP | 3 793 674 | 10/2024 |
| EP | 3 893 957 | 10/2024 |
| EP | 3 914 334 | 10/2024 |
| EP | 3 618 885 | 11/2024 |
| EP | 4 034 221 | 11/2024 |
| EP | 4 087 641 | 11/2024 |
| EP | 4 039 289 | 12/2024 |
| EP | 4 084 856 | 1/2025 |
| EP | 3 522 947 | 2/2025 |
| EP | 4 429 754 | 2/2025 |
| EP | 3 998 102 | 3/2025 |
| EP | 4 429 751 | 3/2025 |
| EP | 4 429 752 | 3/2025 |
| EP | 4 429 753 | 3/2025 |
| EP | 4 023 282 | 4/2025 |
| EP | 3 950 043 | 5/2025 |
| EP | 3 955 986 | 5/2025 |
| EP | 3 958 921 | 5/2025 |
| EP | 3 990 047 | 5/2025 |
| EP | 4 218 900 | 5/2025 |
| EP | 4 429 755 | 5/2025 |
| EP | 2 830 675 | 6/2025 |
| EP | 3 965 845 | 6/2025 |
| EP | 4 039 319 | 6/2025 |
| EP | 3 668 558 | 7/2025 |
| EP | 3 780 041 | 7/2025 |
| EP | 4 095 872 | 7/2025 |
| EP | 3 668 559 | 8/2025 |
| EP | 3 746 149 | 8/2025 |
| EP | 3 823 687 | 8/2025 |
| EP | 3 848 088 | 8/2025 |
| EP | 4 119 184 | 9/2025 |
| EP | 4 218 556 | 9/2025 |
| EP | 4 046 678 | 10/2025 |
| FR | 1458525 | 3/1966 |
| FR | 2 768 056 | 3/1999 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H08-504621 | 5/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515374 | 9/2001 |
| JP | 2001-515375 | 9/2001 |
| JP | 2003-019197 | 1/2003 |
| JP | 2003-525438 | 8/2003 |
| JP | 2003-528697 | 9/2003 |
| JP | 2004-019468 | 1/2004 |
| JP | 2004-278375 | 10/2004 |
| JP | 2005-028137 | 2/2005 |
| JP | 2005-507039 | 3/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6063151 | 1/2017 |
| JP | 6267625 | 1/2018 |
| JP | 2018-057878 | 4/2018 |
| JP | 2019-516458 | 6/2019 |
| JP | 6572056 | 9/2019 |
| JP | 2020-072985 | 5/2020 |
| JP | 2020-523090 | 8/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |

(56)　　　　　References Cited

FOREIGN PATENT DOCUMENTS

| | | |
|---|---|---|
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2014/042925 | 3/2014 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/007120 | 1/2018 |
| WO | WO 2018/036927 | 3/2018 |
| WO | WO 2018/039479 | 3/2018 |
| WO | WO 2018/088939 | 3/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/067233 | 4/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2019/191245 | 10/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/229224 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2020/264174 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2021/191106 | 9/2021 |
| WO | WO 2023/040546 | 12/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/173977 | 8/2022 |
| WO | WO 2022/174249 | 8/2022 |
| WO | WO 2023/226779 | 9/2022 |
| WO | WO 2023/278599 | 1/2023 |
| WO | WO 2023/014742 | 2/2023 |
| WO | WO 2023/049813 | 3/2023 |
| WO | WO 2024/160098 | 4/2023 |
| WO | WO 2023/076461 | 5/2023 |
| WO | WO 2023/076869 | 5/2023 |
| WO | WO 2023/230157 | 11/2023 |
| WO | WO 2024/104184 | 5/2024 |
| WO | WO 2024/243154 | 11/2024 |

OTHER PUBLICATIONS

International Preliminary Report on Patentability and Written Opinion received in PCT Application No. PCT/EP2019/062745, dated Nov. 26, 2020 in 7 pages.
Ai, X. (2013). Radial Bearings. In: Wang, Q.J., Chung, YW. (eds) Encyclopedia of Tribology. Springer, Boston, MA https://doi.org/ 10.1007/978-0-387-92897-5_334, accessed Oct. 18, 2024, pp. 4.

(56)　　　　　References Cited

OTHER PUBLICATIONS

"Edwards SAPIEN 3 Kit—Transapical and Transaortic", Edwards Lifesciences, Released Nov. 8, 2016, pp. 11. chrome-extension://efaidnbmnnnibpcajpcglclefindmkaj/https://edwardsprod.blob.core.windows.net/media/De/sapien3/doc-0045537b%20-%20certitude.pdf.

Escudeiro et al., "Tribological behavior of uncoated and DLC-coated CoCr and Ti-alloys in contact with UHMWPE and PEEK counterbodies;" Tribology International, vol. 89, 2015, pp. 97-104.

GGB by Timken Bearings FAQ; "What is a Slide Bearing?;" https://www.ggbearings.com/en/why-choose-ggb/faq/bearings-faq/what-slide-bearing; accessed Oct. 10, 2024, pp. 1.

Google.com, "Spider Bearing—Search Results;" https://www.google.com/search?q=spider+bearing&rlz=X1C1GCEA_enUS1059US1059&oq=spider+beari&gs_lcrp=EgZjaHJvbWUqCQgAEEUYOxiABDIJCAAQRRg7GIAEMgYIARBFGDkyBwgCEAAYgAQyBwgDEAAYgAQyBwgEEAAYgAQyBwgFEAAYgAQyBwgGEAAYgAQyBggHEEUYPKgCALACAA&sourceid=chrome&ie=UTF-8, accessed Oct. 18, 2024, pp. 4.

Gopinath, Divya, "A System for Impedance Characterization of Coronary Stents", University of Strathclyde Engineering, Thesis, Aug. 2015, pp. 77.

Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.

McMaster-Carr Online Catalog, "Bearings search results;" https://www.mcmaster.com/products/bearings/; accessed Oct. 18, 2024, pp. 5.

McMaster-Carr Online Catalog, "Slide Bearings search results;" https://www.mcmaster.com/products/slide-bearings/; accessed Oct. 18, 2024, pp. 21.

Neale, Michael J., "The Tribology Handbook;" 1999, Butterworth-Heinemann, Second Edition, pp. 582.

Park et al., "A Novel Electrical Potential Sensing Method for in Vitro Stent Fracture Monitoring and Detection", Jan. 1, 2011, vol. 21, No. 4, pp. 213-222.

Rbcbearings.com, "RBC Bearings Incorporated—Products;" https://www.rbcbearings.com/Products; accessed Oct. 18, 2024, pp. 2.

Sak et al., "Influence of polyetheretherketone coatings on the Ti—13Nb—13Zr titanium alloy's bio-tribological properties and corrosion resistance;" Materials Science and Engineering: C, vol. 63, 2016, pp. 52-61.

SKF.com; "Products: Bearings;" https://www.skf.com/us/products/bearings; accessed Oct. 18, 2024, pp. 8.

Wikipedia, "Plain Bearing," https://en.wikipedia.org/wiki/Plain_bearing; accessed Oct. 18, 2024, pp. 10.

"ABMD—Taking a Closer Look at Impella ECP as the Pivotal Trial Gets Underway", Guggenheim, Press Release, Mar. 29, 2022, pp. 4.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Delgado et al., "Interventional Treatment of Advanced Ischemic Heart Disease", Percutaneous Mechanical Assist Devices, Ch. 6, Springer, 2009, pp. 85-91.

Delgado et al., "Interventional Treatment of Advanced Ischemic Heart Disease", The Future of Treatment of Advanced Ischemic Heart Disease, Ch. 8, Springer, 2009, pp. 129-142.

Eeckhout, MD, PhD, et al., "Handbook of Complications During Percutaneous Cardiovascular Interventions", 2007 Informa UK Ltd., Ch. 12, pp. 167-177.

"FDA Approves Abiomed's Heart Pump Impella, Shares Rise", Reuters 2008 press release, Jun. 2, 2008, https://jp.reuters.com/article/us-abiomed/fda-approves-abiomeds-heart-pump-impella-shares-rise-idUSBNG131420080602/, 1 page.

Lake et al., "Pediatric Cardiac Anesthesia", 4th Edition, 2005, Ch. 15, pp. 291-303.

Machiraju, Venkat R., "Redo Cardiac Surgery in Adults", Practical Approaches to the Current "On-Pump" Redo Coronary Artery Bypass Surgery, Ch. 2, Springer, 2012, pp. 7-19.

Machiraju, Venkat R., "Redo Cardiac Surgery in Adults", Options for Advanced Mechanical Support for Cardiogenic Shock Complicating Cardiac Reoperations, Ch. 9, Springer, 2012, pp. 67-80.

Machiraju, Venkat R., "Redo Cardiac Surgery in Adults", Percutaneous Approaches to Valvular Heart Disease After Previous Cardiac Surgery, Ch. 21, Springer, 2012, pp. 195-200.

Parrillo et al., "Critical Care Medicine", Principles of Diagnosis and Management in the Adult, Elsevier, 4th Edition, 2014, Chapters 4 & 29, pp. 47-58.e1 and 442-469.e4.

Vincent, MD, Phd, et al., "Textbook of Critical Care", Acute Coronary Syndromes: Therapy, Elsevier, 7th Edition, Ch. 78, 2017, pp. 520-531.e3.

Vincent, MD, PhD, et al., "Textbook of Critical Care", Mechanical Support in Cardiogenic Shock, Elsevier, 7th Edition, Ch. 91, 2017, pp. 637-648.e3.

* cited by examiner

Assemble at Least Four Shell Elements

ROTOR, MAGNETIC COUPLING DEVICE, ELECTRIC MOTOR FOR A CARDIAC SUPPORT SYSTEM, PUMP UNIT FOR A CARDIAC SUPPORT SYSTEM, AND METHOD FOR PRODUCING A ROTOR

BACKGROUND

Field

The invention relates to a rotor, a magnetic coupling device, an electric motor for a cardiac support system, a pump unit for a cardiac support system, and a method for producing a rotor.

Description of the Related Art

Conventional magnetic coupling elements often have limitations with respect to magnetization density. This can lead to unfavorable magnetic coupling behavior and, in particular in application scenarios in which the available installation space is small, such as in medical devices that are to be implanted in the body of a patient, makes said elements disadvantageous.

SUMMARY

The object of the invention is to create a rotor which can be used in a magnetic coupling device, in an electric motor for a cardiac support system and/or in a pump unit for a cardiac support system, and which enables the provision and/or transmission of high torques in a small installation space.

This object is achieved by the rotor described herein. Advantageous embodiments of the invention are described herein.

The rotor according to the invention and described herein is in particular suitable for use in a cardiac support system. A rotor according to the invention is or can be assembled from at least four shell elements to form a hollow cylinder and/or on a shaft, wherein the shell elements are or can be magnetized alternately in oppositely directed or orthogonal magnetization directions in order to form a magnetic body having at least four magnetic poles.

Shell elements in the present case can, for example, be permanent magnets or ferromagnetic or magnetizable elements which are or can be magnetized in a predetermined magnetization direction. The shell elements here are magnetized, for example, before they are assembled to form the rotor. The shell elements can furthermore be disposed such that adjacent shell elements are magnetized in oppositely directed or orthogonal magnetization directions.

The invention is based on the knowledge that a very high magnetization density and thus a high magnetic flux can be achieved, because a rotor can be formed by using shell elements that are disposed in such a way that adjacent shell elements are poled in oppositely aligned or orthogonal magnetization directions. In this way, a high magnetic flux can be ensured on the surface of the rotor, which can then be used to achieve a high magnetic frictional connection to a further magnetic element opposite to the rotor, so that, for example, a magnetic coupling device capable of transmitting high torques can be created.

One advantageous embodiment of the invention provides that, in the assembled state of the rotor, a first shell element and a second shell element are disposed opposite one another to form a first pole pair, and a third shell element and a fourth shell element are disposed opposite one another to form a second pole pair. The advantage of this is that opposite shell elements form a respective pair of poles, so that a high magnetic flux through the rotor and over a surface of the rotor can be produced.

In a further advantageous embodiment of the invention, the first shell element is or can be parallel magnetized in a first magnetization direction, the second shell element is or can be parallel magnetized in a second magnetization direction opposite to the first magnetization direction, the third shell element is or can be parallel magnetized in a third magnetization direction orthogonal to the first magnetization direction and the second magnetization direction and the fourth shell element is or can be parallel magnetized in a fourth magnetization direction opposite to the third magnetization direction. The advantage of such an embodiment is that a very high magnetic flux density can be realized on an outer surface of the rotor, so that high torque transmission is made possible with such a rotor. The anisotropy of the material of the shell elements with respect to the magnetization can thus be compensated very efficiently.

An embodiment of the invention in which the shell elements are or can be radially magnetized has a particularly high magnetic flux density. The advantage of such an embodiment is that the magnetic flux lines of the shell elements emerge substantially perpendicularly on an outer surface of the rotor, so that a homogeneous, radial magnetic field can be produced around the rotor, which enables a favorable and efficient transmission of torque.

According to a further embodiment of the approach proposed here, the rotor can also comprise a shaft, whereby the shaft and the magnetic body are or can be connected to one another in a torsionally rigid manner. The magnetic body can be glued or pressed onto the shaft, for example. Such an embodiment permits cost-effective production of a magnetically very effective rotor.

An embodiment of the invention in which the rotor has a diameter less than 20 mm, in particular less than 10 mm, is particularly efficient. The advantage of such an embodiment is that, on the one hand, such a rotor can be manufactured very easily and, on the other hand, it enables a very high transmission of torque compared to known magnetic coupling elements or rotors.

A magnetic coupling device according to the invention has the following features:

a rotor according to a variant presented here; and a further magnetic body, which is or can be assembled from at least four further shell elements to form a hollow cylinder, wherein the further shell elements are or can be magnetized in oppositely directed magnetization directions to form at least four further magnetic poles, wherein the magnetic body of the rotor and the further magnetic body are or can be disposed one inside the other, in particular are or can be disposed concentrically to one another, and are or can be mounted so as to be rotatable relative to one another.

Such a magnetic coupling device enables very efficient transmission of torque, in particular in very small installation spaces, by producing a high flux density between the rotor and the further magnetic body.

According to a preferred embodiment of the invention, the magnetic body and the further magnetic body can in particular each have the same number of magnetic poles. This enables particularly efficient guidance of the magnetic field, which is characterized by a high ability to transmit torque.

According to a further embodiment of the invention, the further magnetic body is or can also be assembled from at least four additional shell elements to form the hollow body, wherein, in the assembled state of the further magnetic body, each one of the four additional shell elements is respectively disposed between two of the four further shell elements, wherein each of the four additional shell elements is or can be magnetized in tangential direction, for example to form a Halbach-Array. Such an embodiment of the approach proposed here offers the advantage that the additional shell elements, each of which is or can be magnetized in tangential direction, enable efficient guidance of magnetic lines in the further magnetic body in order to, if possible, prevent the magnetic field lines from escaping from the further magnetic body. It is thus possible to ensure a high magnetic flux between the rotor and the further magnetic body formed as a hollow cylinder, which consequently again enables a very efficient transmission of torque between the rotor and the further magnetic body or the hollow body.

The invention also extends to an electric motor comprising a rotor according to a variant presented here and/or a magnetic coupling device according to a variant presented here. The aforementioned advantages can be realized or implemented very efficiently with such an embodiment as well.

The invention in particular extends to a pump unit for a cardiac support system, wherein the pump unit comprises a rotor according to a variant presented here and/or a magnetic coupling device according to a variant presented here. Such a pump unit for a cardiac support system in particular requires high torque transmission in a small available installation space, so that the approach presented here can be used particularly favorably in such an application scenario in a patient.

The invention furthermore also extends to a method for producing a rotor having the features specified above, wherein the method comprises the following steps:

Assembling at least four shell elements alternately in oppositely directed or orthogonal magnetization directions to form a hollow cylinder and/or on a shaft, in order to form a magnetic body having at least four magnetic poles, in order to produce the rotor.

Such an embodiment, too, makes it possible to realize the aforementioned advantages in a technically simple, cost-effective and efficient manner.

This method can be implemented in software or hardware, for example, or in a combination of software and hardware, for example in a control device.

The approach presented here further creates a device which is configured to carry out, control or implement the steps of a variant of a method presented here in corresponding facilities. The underlying object of the invention can likewise be achieved quickly and efficiently using this design variant of the invention in the form of a device.

For this purpose, the device can comprise at least one computation unit for processing signals or data, at least one memory unit for storing signals or data, at least one interface to a sensor or an actuator for inputting sensor signals from the sensor or for outputting data or control signals to the actuator, and/or at least one communication interface for inputting or outputting data embedded in a communication protocol. The computation unit can be a signal processor, a microcontroller or the like, for example, whereas the memory unit can be a flash memory, an EPROM or a magnetic memory unit. The communication interface can be configured to input or output data in a wireless and/or a wired manner, whereby a communication interface that can input or output wired data can, for example, input said data electrically or optically from a corresponding data transmission line or output it into a corresponding data transmission line.

In the present case, a device can be an electrical device that processes sensor signals and outputs control and/or data signals as a function of said signals. The device can comprise an interface that can be hardware and/or software-based. In the case of a hardware-based configuration, the interfaces can be part of a so-called system ASIC, for example, which contains the various functions of the device. However, it is also possible for the interfaces to be separate, integrated circuits or consist at least in part of discrete components. In the case of a software-based configuration, the interfaces can be software modules that are, for example, provided on a microcontroller alongside other software modules.

A computer program product or computer program with program code, which may be stored on a machine-readable carrier or storage medium such as a semiconductor memory, a hard drive memory or an optical memory, and is used to carry out, implement and/or control the steps of the method according to one of the above-described embodiments, is also advantageous, in particular if the program product or program is executed on a computer or device.

BRIEF DESCRIPTION OF THE DRAWINGS

Advantageous design examples of the invention are shown in the drawings and explained in more detail in the following description.

The figures show.

DETAILED DESCRIPTION

In the following description of favorable design examples of the present invention, the same or similar reference signs are used for elements shown in the various figures and having a similar effect; a repeated description of these elements is omitted.

Figure 1A:
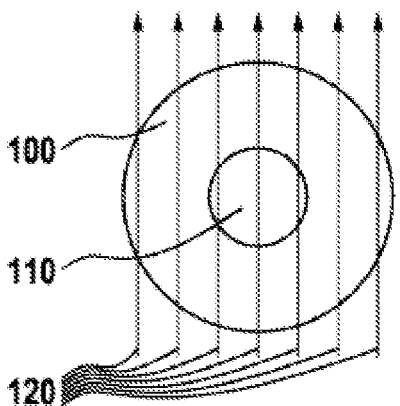
FIG. 1A a cross-sectional illustration of a rotor which is disposed on or glued onto a shaft of a motor.

FIG. 1A shows a cross-sectional illustration of a rotor 100, which is disposed on or glued onto a shaft 110 of a motor. The rotor 100 here is configured as a hollow cylinder. Also shown are magnetic field lines 120 which act on the magnetizable element(s) of the rotor 100 in order to magnetize the rotor. The magnetic field lines, which have been provided with the reference sign 120, can also be understood as magnetization directions at the respective positions on the rotor 100.

Figure 1B:
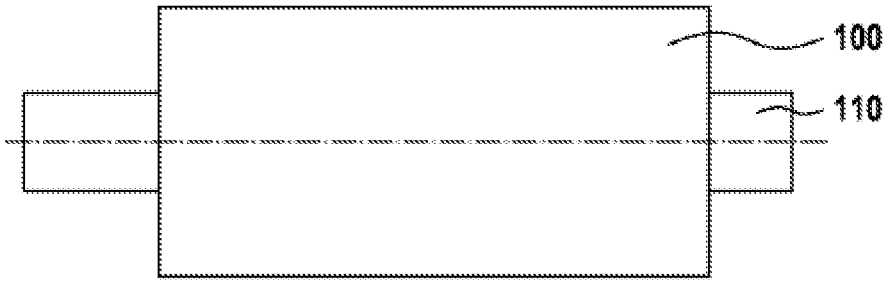
FIG. 1B a side view of the rotor which is disposed on or glued onto the shaft.

FIG. 1B shows a side view of the rotor 100, which is disposed on or glued onto the shaft 110. The rotor 100 can have a magnet length of 10 mm, a magnet height of 1 mm and/or a shaft diameter of 1 mm, for example. The rotor 100 can, for example, be used as a component of a magnetic coupling of a cardiac support system to make the best possible use of the available installation space in the patient's body or artery.

Magnetic couplings and electric motors having very small diameters in the range of less than approximately 20 mm use axles (such as the shaft 110 here in FIGS. 1A and 1B) having permanent magnets attached to the axle, the so-called rotors 100, which can also comprise further structural elements such as magnetic returns (yokes) between the shaft or bearings pressed onto the shaft.

Due to the required or desired performance, these permanent magnets are preferably made of magnetic materials having a very high energy density. One characteristic of these magnetic materials is the strong anisotropy of the magnets with respect to the magnetization direction. This is used to make the best possible use of the material with respect to the achievable energy density in the magnet or to achieve the highest possible magnetic flux density in the magnetic circuit of the electric motors or magnetic couplings.

The manufacturing processes for permanent magnets having a very high energy density result in relatively large tolerances in the magnet dimensions. In the case of very small magnet dimensions in the rotors 100, this leads to relatively large tolerances in the components having the magnets. For this reason, the rotors 100 of small motors or couplings are preferably made of hollow-cylindrical permanent magnets, which are pushed and glued directly onto the non-magnetic or soft magnetic shaft. For the required high energy densities and two-pole couplings or electric motors, the initial magnetization process is performed diametrically across the entire cylinder in order to make optimum use of the anisotropy of the magnetic material, as shown in FIG. 1A.

Figure 2:
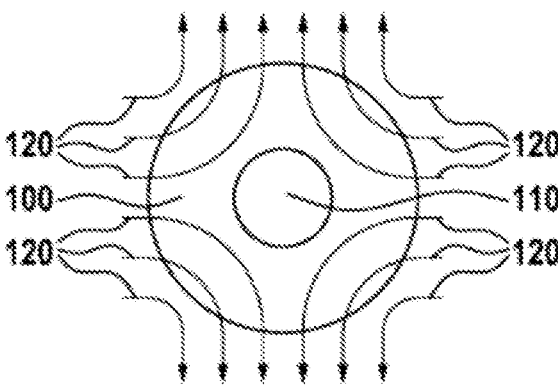
FIG. 2 a cross-sectional illustration of a rotor which is disposed on or glued onto a shaft of a motor, whereby a four-poled magnet is now formed as a rotor by impressing the magnetic field lines.

FIG. 2 shows a cross-sectional illustration of a rotor 100, which is disposed on or glued onto a shaft 110 of a motor, whereby a four-poled magnet is now formed as the rotor 100 by impressing the magnetic field lines 120 according to the illustration of FIG. 2. Therefore, a four-poled magnetic field is used to magnetize hollow-cylindrical permanent magnets. A magnetization for impressing 4 poles, as shown in FIG. 2, in such anisotropically prepressed magnet hollow cylinders leads to an uneven magnetic flux in the preferably orthogonal magnetization directions. This is not advantageous for the mentioned components, because the magnetic material is not fully utilized. If magnets without a preferred direction are used, owing to the principle involved only a comparatively lower energy density can be achieved, and consequently a smaller magnetic flux in the magnetic circuit of a coupling or an electric motor. This applies accordingly to higher pole numbers. In the typical design and manufacturing method, the available torque for both components drops sharply as a result of the small rotor diameter. Under the same boundary conditions (drive voltage and drive current), the maximum speed of electric motors can then become very high. For applications in which the focus is not so much on very high speeds, in which a high torque is more important, gears can be added to the drive train to shift the mechanical performance from high speeds and low torques to lower speeds and higher torques. This requires at least one further component and additional installation space. In certain applications, both implications are undesirable or simply not possible. This is the case for a left ventricular cardiac support system, which is placed in the aorta, for example, or completely or partially in the left ventricle.

To increase the performance of such coupling elements, it is useful to create a greater magnetic flux in the magnetic circuit. In many applications it is expedient to do this by achieving a higher torque. Advantageously, the number of pole pairs can be increased in order to achieve higher torques.

Since, as described above, this is not or only conditionally possible for hollow-cylindrical magnets at the required high energy densities and small dimensions, the proposal here, according to a design example of the invention, is to produce the required magnetic flux using magnetic shells, which are for example also segmented in tangential direction, as the shell elements that can be glued onto a shaft or a magnetic yoke.

Figure 3A:
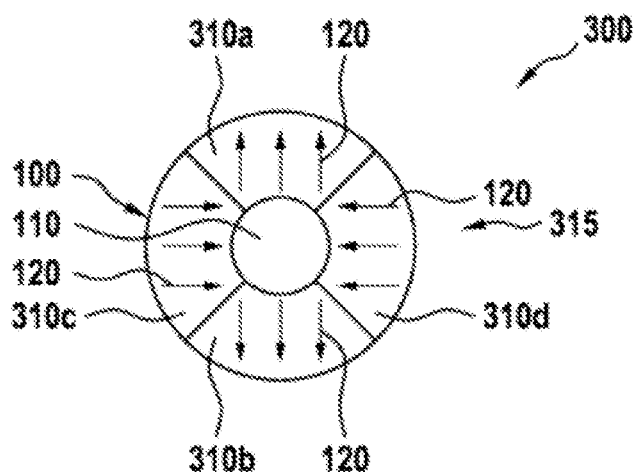
FIG. 3A a cross-sectional illustration of a rotor according to a design example of the present invention.

FIG. 3A shows a cross-sectional illustration of a magnetic coupling element 300 having a rotor 100 according to a design example of the present invention. The rotor 100 is formed here by at least four shell elements 310a, 310b, 310c and 310d, which are assembled to form a magnetic body 315, for example in the form of a hollow cylinder, and/or to be fixed on the shaft 110 in a non-rotatable manner. The shell elements 310a-d are disposed such that the individual shell elements 310a-d are or can be magnetized alternately in opposite or orthogonal directions. For this purpose, the shell elements 310a, 310b, 310c and 310d are made of a hard magnetic or ferromagnetic material or are already directly magnetized as permanent magnets. In FIG. 3A, this alignment of the magnetization is illustrated by the schematically drawn magnetic field lines 120, which now correspond to the magnetic field lines 120 caused by a magnetic field produced by the respective shell elements 310 themselves as permanent magnets. FIG. 3A shows, in particular, that the first shell element 310a is polarized such that the magnetic field lines 120 of this shell element 310a point upward, whereas the magnetic field lines 120 of the third shell element 310c, which adjoins the first shell element 310a on the left, point to the right and are thus aligned orthogonally to the magnetic field lines 120 of the first shell element 310a. The magnetic field lines 120 of the second shell element 310b, which adjoins the third shell element 310c at the bottom, point downward and thus in a direction opposite to the direction of the magnetic field lines 120 of the first shell element 310a. The magnetic field lines 120 of the fourth shell element 310d, which adjoins the second shell element 310a on the right, are directed to the left and thus orthogonal to the magnetic field lines 120 of the first and second shell element 310a and 310b. The magnetic field lines 120 of the fourth shell element 310d point in a direction opposite to the direction of the magnetic field lines 120 of the third shell element 310c. Thus, FIG. 3A shows a four-poled rotor 100 comprising shell elements 310 or shell magnets with parallel magnetization which are disposed or mounted on the shaft 110.

Figure 3B:
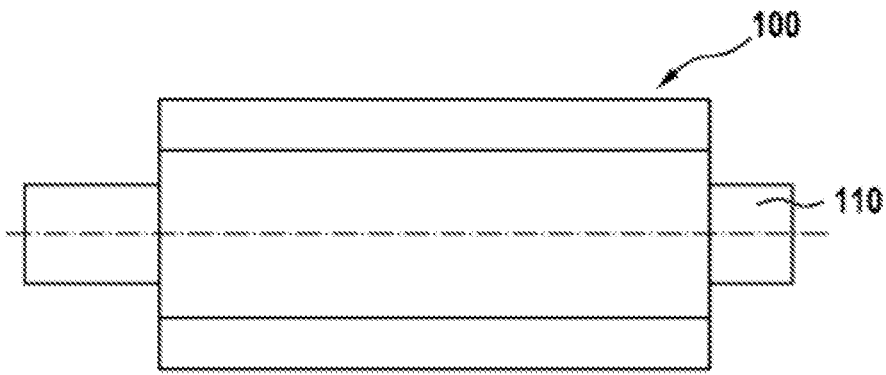
FIG. 3B a side view of the rotor of FIG. 3A which is disposed on or glued onto the shaft.

FIG. 3B shows a side view of the rotor 100 of FIG. 3A, which is disposed on or glued onto the shaft 110. The rotor 100 can again have a magnet length (shell element length) of 10 mm, a magnet height of 1 mm and/or a shaft diameter of 1 mm, for example. The rotor 100 can, for example, be used as a component of a magnetic coupling of a cardiac support system to make the best possible use of the available installation space in the patient's body or artery.

In the approach shown in FIGS. 3A and 3B, the shell elements 310a to 310d, which, in terms of dimensions, are identical magnetic shells for example, are preferably magnetized in parallel, for example alternately in radially positive or radially negative direction. A given anisotropy of the magnetic shells or shell elements 310a to 310d can thus be optimally utilized to maximize the magnetic flux in the magnetic circuit.

Figure 4:
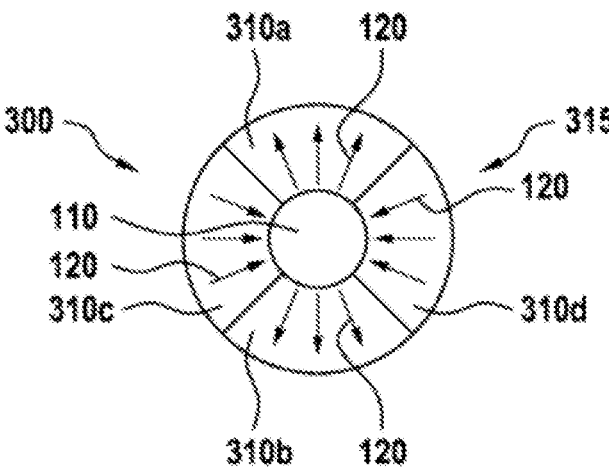
FIG. 4 a cross-sectional illustration of a rotor according to a further design example of the present invention.

FIG. 4 shows a cross-sectional illustration of a magnetic coupling element 300 having a rotor 100 according to a further design example of the present invention. It is thus possible to realize a radial magnetization, but in which, with the same dimensions, a slightly smaller magnetic flux occurs in the magnetic flux compared to the magnetization according to the illustration of FIG. 3A. In such a radial magnetization, the magnetic field lines 120 are aligned radially toward the shaft 110 or away from the shaft 110, so that there are no parallel magnetic field lines 120. Rather, the magnetic field lines 120 enter or exit perpendicularly from a surface of the shell elements 310a to 310d. Such a magnetization can also be produced in a technically simple manner, for example via a core as a shaft 110 which is used to magnetize the shell elements 31q0a [sic] to 310d. In this design example, the magnetic field lines 120 of adjacent shell elements 310a to 310d furthermore extend in an opposite direction, for example, whereas the magnetic field lines 120 of adjacent shell elements 310a to 310d are aligned orthogonally to one another as shown in the illustration of FIG. 3A.

The number of pole pairs of a rotor 100 or a magnetic body can be two or more. By using magnetic materials having the smallest possible grain size and, if necessary, reworking, the loss of magnet mass can be kept small while maintaining the same external dimensions of the components or shell elements 310. In rotors 110 having pole pair numbers greater than one, the amount of energy for torque transmission, which is in principle lower due to the smaller magnet mass resulting from the tolerances, is more than compensated by the better utilization of the magnetic material due to the use of anisotropic material.

Figure 5:
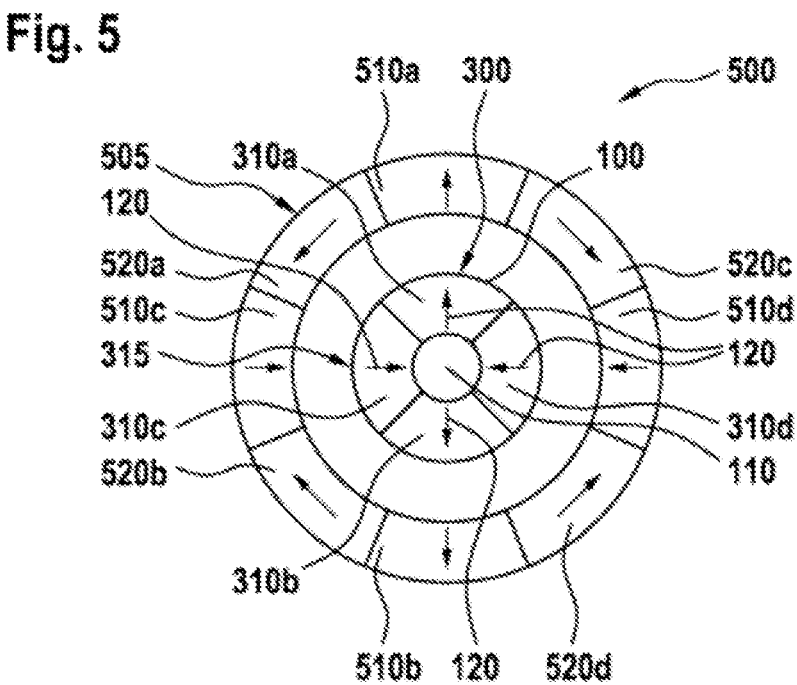
FIG. 5 a cross-sectional illustration of a magnetic coupling device according to a further design example of the present invention comprising a rotor.

FIG. 5 shows a cross-sectional illustration of a magnetic coupling device 500 according to a further design example of the present invention comprising a magnetic coupling element 300 having a rotor 100 as described above, for example. In this magnetic coupling element 300, the shell elements 310a to 310d of the rotor 100 are formed according to the illustration of FIG. 3A; i.e. with adjacent shell elements 310 comprising magnetic field lines 120 which aligned orthogonally to one another. The magnetic coupling device 500 also comprises a further magnetic body 505, which is hollow-cylindrical, for example, and comprises at least four further shell elements 510a, 510b, 510c and 510d. The further shell elements 510a to 510d are or can be magnetized in oppositely directed magnetization directions corresponding to the magnetic field lines 120 in order to form at least four further magnetic poles. Furthermore, the magnetic body of the rotor 100 and the further magnetic body 500 are or can be disposed one inside the other, in particular are or can be disposed concentrically to one another, and are or can be mounted so as to be rotatable relative to one another. An orientation of the magnetic field lines 120 of the further shell elements 510a to 510d can correspond to the orientation of the magnetic field lines 120 of the shell elements 310a to 310d. For example, the orientation of the magnetization of the further shell elements

510a to 510b can correspond to the orientation of the shell elements 310a to 310d according to the illustration of FIG. 3A.

It is thus possible to realize a magnetic coupling device 500, which enables a very efficient utilization of the magnetization of the materials for the rotor 100 and a hollow cylinder as a further magnetic body 505 and thus opens up an efficient torque transmission of a torque from the shaft 110 to the hollow cylinder.

A design example of the approach presented here, which, as shown in FIG. 5, comprises four additional shell elements 520a, 520b, 520c and 520d, is particularly advantageous. In the assembled state of the further magnetic body 505, each one of these four additional shell elements 520a, 520b, 520c, 520d is respectively disposed between two of the four additional shell elements 510a to 510d, wherein each of the four additional shell elements 520a to 520d is or can be magnetized in tangential direction. A shell element 520a to 520d can be considered to be a shell element 520a to 520d magnetized in tangential direction if the magnetization, or a magnetic field line 120 caused by such magnetization, of said shell element 520a to 520d is aligned tangentially to an outer surface with respect to a further magnetic body 505 configured as a hollow cylinder. It is thus now possible to guide a magnetic flux in the further magnetic body 505 such that a high flux density of the magnetic field between the further magnetic body 505 and the magnetic coupling element 300 or rotor 100 can be achieved, which in turn leads to an efficient coupling of the further magnetic body 505 and the rotor 110 or the magnetic coupling element. Thus, a tangentially segmented, multi-pole magnetic axis for miniaturized magnetic couplings and electric motors is presented here as well, in particular for use in a pump of a cardiac support system.

FIG. 5 therefore shows an outer magnet ring having the same number of pole pairs as in the rotor 100, here as a design with a Halbach array. In principle, with the higher pole pair number, the thus increased magnetic flux in the magnetic circuit produces a greater torque in said components compared to two-poled rotors or multi-poled rotors made of hollow-cylindrical magnets. In electric motors, the winding should be adapted accordingly to accommodate the higher number of pole pairs. In radial magnetic couplings, the outer hollow-cylindrical magnet must also be adapted to the pole number. The outer hollow cylinder can optionally consist of a solid cylinder, joined magnetic shells corresponding to the magnetic shells on the rotor 110, or a Halbach array as shown in FIG. 5.

Such a rotor design can advantageously be used, in particular in left ventricular cardiac support systems (LVAD). In principle, however, all applications requiring high power density and/or high torque are predestined for this type of rotor design.

Figure 6:
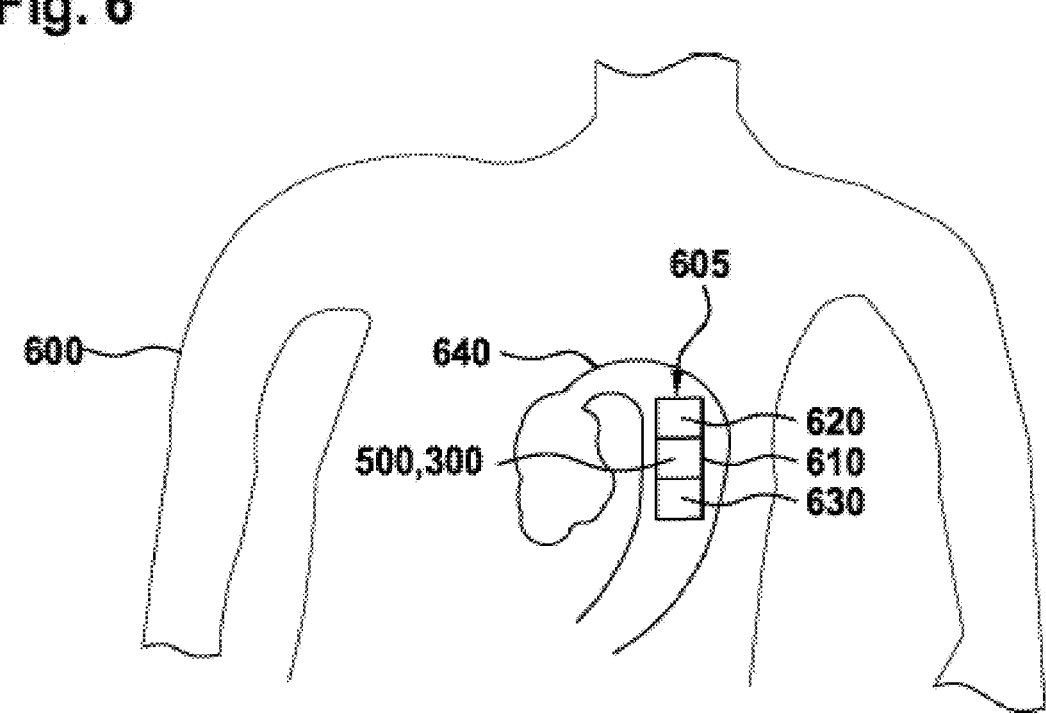
FIG. 6 a schematic illustration of a patient implanted with a cardiac support system comprising a magnetic coupling device or a rotor according to a design example of the invention.

FIG. 6 shows an illustration of a patient 600 implanted with a cardiac support system 605. The cardiac support system 605 includes a pump unit 610, which comprises a magnetic coupling device 500 for coupling an electric motor 620 to an impeller 630 for conveying blood of the patient 600 and wherein the pump unit 610 is implanted, for example in an aorta 640 of the patient 600.

Figure 7:
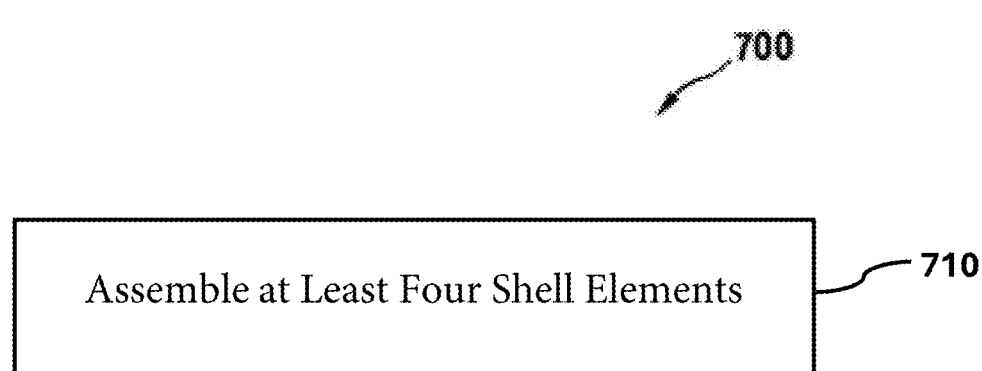
FIG. 7 a flow diagram of a method for producing a rotor according to a design example.

FIG. 7 shows a flow diagram of a method 700 for producing a rotor according to a design example described here, wherein the method 700 includes a step 710 of assembling at least four shell elements alternately in oppositely directed or orthogonal magnetization directions to form a hollow cylinder and/or on a shaft, in order to form a magnetic body having at least four magnetic poles, in order to produce the rotor.

If a design example includes an "and/or" conjunction between a first feature and a second feature, this should be read to mean that the design example according to one embodiment comprises both the first feature and the second feature and, according to another embodiment, comprises either only the first feature or only the second feature.

The invention claimed is:

1. A pump unit for a cardiac support system, the pump unit comprising:
    an electric motor comprising a shaft; and
    a magnetic coupling device comprising:
        a rotor comprising a first magnetic body disposed on the shaft, the first magnetic body comprising a first plurality of shell elements, wherein a first subset of the first plurality of shell elements are magnetized in radially opposite magnetization directions, and the first magnetic body comprising at least four magnetic poles; and
        a second magnetic body comprising a second plurality of shell elements, wherein a first subset of the second plurality of shell elements are magnetized in opposing directions to form at least four magnetic poles,
        wherein a second subset of the second plurality of shell elements are magnetized in directions tangential to an outer surface of the second magnetic body; and
        when assembled, each shell element of the second subset of the second plurality of shell elements is positioned between two adjacent shell elements of the first subset of the second plurality of shell elements; and
      wherein the first magnetic body is positioned concentrically inside the second magnetic body.

2. The pump unit of claim 1 comprising an impeller configured to convey blood of a patient, wherein the magnetic coupling device is configured to couple the electric motor to the impeller.

3. The pump unit of claim 1, wherein the first magnetic body and the shaft are connected to one another in a torsionally rigid manner.

4. The pump unit of claim 1, wherein the first magnetic body and the second magnetic body are rotatable relative to one another.

5. The pump unit of claim 1, wherein the first plurality of shell elements are configured to form a hollow cylinder.

6. The pump unit of claim 1, wherein the first plurality of shell elements are permanent magnets.

7. The pump unit of claim 1, wherein the first plurality of shell elements comprises a first shell element, a second shell element, a third shell element, and a fourth shell element, and wherein the first shell element and the second shell element are arranged opposite to one another to form a first pole pair, and the third shell element and the fourth shell element are arranged opposite to one another to form a second pole pair.

8. The pump unit of claim 7, wherein:
    the first shell element is magnetized in a first magnetization direction;
    the second shell element is magnetized in a second magnetization direction opposite to the first magnetization direction;
    the third shell element is magnetized in a third magnetization direction orthogonal to the first magnetization direction and the second magnetization direction; and
    the fourth shell element is magnetized in a fourth magnetization direction opposite to the third magnetization direction.

9. The pump unit of claim 1, wherein the rotor has a diameter smaller than 20 mm.

10. The pump unit of claim 1, wherein the electric motor further comprises a winding adapted to the at least four magnetic poles of the first magnetic body.

11. The pump unit of claim 1, wherein the second magnetic body comprises a magnetic ring configured as a Halbach array.

12. The pump unit of claim 1, wherein the second plurality of shell elements are configured to form a hollow cylinder.

13. The pump unit of claim 1, wherein the first magnetic body and the second magnetic body each comprise the same number of magnetic poles.

14. The pump unit of claim 1, wherein the first plurality of shell elements are glued directly onto the shaft.

15. The pump unit of claim 1, wherein the first plurality of shell elements are comprised of a ferromagnetic material.

* * * * *